(12) United States Patent
Tonge et al.

(10) Patent No.: US 11,857,352 B2
(45) Date of Patent: Jan. 2, 2024

(54) POSITRON IMAGING TOMOGRAPHY IMAGING AGENT COMPOSITION AND METHOD FOR BACTERIAL INFECTION

(71) Applicant: The Research Foundation for the State University of New York, Albany, NY (US)

(72) Inventors: Peter Tonge, Setauket, NY (US); Zhuo Zhang, Coram, NY (US); Peter Smith-Jones, Port Jefferson, NY (US); Li Liu, Stony Brook, NY (US); Hui Wang, Woodside, NY (US)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 471 days.

(21) Appl. No.: 16/330,679

(22) PCT Filed: Sep. 6, 2017

(86) PCT No.: PCT/US2017/050248
§ 371 (c)(1),
(2) Date: Mar. 5, 2019

(87) PCT Pub. No.: WO2018/048882
PCT Pub. Date: Mar. 15, 2018

(65) Prior Publication Data
US 2019/0209103 A1 Jul. 11, 2019

Related U.S. Application Data

(60) Provisional application No. 62/518,674, filed on Jun. 13, 2017, provisional application No. 62/383,779, filed on Sep. 6, 2016.

(51) Int. Cl.
| | |
|---|---|
| *C07C 229/60* | (2006.01) |
| *C07C 227/12* | (2006.01) |
| *A61B 6/03* | (2006.01) |
| *C07B 59/00* | (2006.01) |
| *A61K 51/04* | (2006.01) |
| *A61P 31/04* | (2006.01) |

(52) U.S. Cl.
CPC .......... *A61B 6/037* (2013.01); *A61K 51/0402* (2013.01); *A61P 31/04* (2018.01); *C07B 59/001* (2013.01); *C07C 227/12* (2013.01); *C07C 229/60* (2013.01)

(58) Field of Classification Search
None
See application file for complete search history.

(56) References Cited

U.S. PATENT DOCUMENTS

| | | |
|---|---|---|
| 5,514,676 A | 5/1996 | Ulrich et al. |
| 7,888,330 B2 | 2/2011 | Shields |
| 7,998,979 B2 | 8/2011 | Guillemont |
| 8,071,605 B2 | 12/2011 | Basarab |
| 8,106,031 B2 | 1/2012 | Lee |
| 8,173,657 B2 | 5/2012 | Sutton |
| 8,217,058 B2 | 7/2012 | Patel |
| 8,283,361 B2 | 10/2012 | Choy |
| 8,293,732 B2 | 10/2012 | Guillemont |
| 8,357,486 B2 | 1/2013 | Stritzker |
| 8,415,475 B2 | 4/2013 | Guillemont |
| 8,624,022 B2 | 1/2014 | Carr |
| 8,853,258 B2 | 10/2014 | Brown |
| 9,133,167 B2 | 9/2015 | Guillemont |
| 9,493,489 B2 | 11/2016 | Jacobs et al. |
| 9,556,114 B2 | 1/2017 | Duggan |
| 9,617,244 B2 | 4/2017 | Guillemont |
| 10,035,813 B2 | 7/2018 | Partridge |
| 10,294,271 B1 | 5/2019 | Manning |
| 10,383,960 B2 | 8/2019 | Williamson |
| 10,428,105 B2 | 10/2019 | Fenaux |

(Continued)

FOREIGN PATENT DOCUMENTS

| | | |
|---|---|---|
| WO | WO2003072534 | 9/2003 |
| WO | WO 2010/035166 A1 | 4/2010 |

(Continued)

OTHER PUBLICATIONS

International Preliminary Report on Patentability dated Dec. 3, 2019 in connection with the PCT International Application No. PCT/US2017/050248.

(Continued)

*Primary Examiner* — Sudhakar Katakam
*Assistant Examiner* — Jennifer C Sawyer
(74) *Attorney, Agent, or Firm* — Gary J. Gershik

(57) ABSTRACT

The present invention provides a composition comprising the compound having the structure:

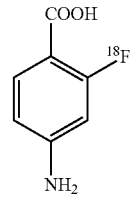

or a salt of the compound; 4-amino-2-[$^{19}$F]-fluorobenzoic acid or a salt of 4-amino-2-[$^{19}$F]-fluorobenzoic acid; and at least one acceptable carrier.

5 Claims, 8 Drawing Sheets

(56) References Cited

U.S. PATENT DOCUMENTS

| | | | |
|---|---|---|---|
| 10,654,852 | B2 | 5/2020 | Vacca |
| 10,829,440 | B2 | 11/2020 | Basu |
| 10,835,625 | B2 | 11/2020 | Sellmyer |
| 10,881,749 | B2 | 1/2021 | Namavari |
| 10,933,051 | B2 | 3/2021 | Choi |
| 11,065,350 | B2 | 7/2021 | Dunphy |
| 11,103,605 | B2 | 8/2021 | Donnelly |
| 11,229,713 | B2 | 1/2022 | Donnelly |
| 11,419,335 | B2 | 8/2022 | Huigens |
| 11,511,000 | B2 | 11/2022 | Donnelly |
| 2014/0314671 | A1 | 10/2014 | Namavari et al. |
| 2015/0250906 | A1* | 9/2015 | Jain .................... A61K 51/0402 424/1.89 |

FOREIGN PATENT DOCUMENTS

| | | |
|---|---|---|
| WO | WO 2010/132615 A1 | 11/2010 |
| WO | WO2014052471 | 4/2014 |

OTHER PUBLICATIONS

Adams Dave J. et al., "Nucleophilic routes to selectively fluorinated aromatics", Chem. Soc. Rev., 1999, 28, pp. 225-231.

Written Opinion of the International Searching Authority dated Dec. 14, 2017 in connection with PCT International Application No. PCT/US2017/050248.

International Search Report dated Dec. 14, 2017 in connection with PCT International Application No. PCT/US2017/050248.

Ordonez AA, Weinstein EA, Bambarger LE, Saini V, Chang YS, DeMarco VP, Klunk MH, Urbanowski ME, Moulton KL, Murawski AM, Pokkali S, Kalinda AS, Jain SK. A Systematic Approach for Developing Bacteria-Specific Imaging Tracers. J Nucl Med. Jan. 2017;58(1):144-150. doi: 10.2967/jnumed.116.181792. Epub Sep. 15, 2016. PMID: 27635025; PMCID: PMC5209639.

* cited by examiner

POSITRON IMAGING TOMOGRAPHY IMAGING AGENT COMPOSITION AND METHOD FOR BACTERIAL INFECTION

CROSS-REFERENCE TO RELATED APPLICATIONS

This application is a § 371 national stage of PCT International Application No. PCT/US2017/050248, filed Sep. 6, 2017 and claims priority of U.S. Provisional Application Nos. 62/518,674, filed Jun. 13, 2017 and 62/383,779, filed Sep. 6, 2016, the contents of each of which are hereby incorporated by reference into the application.

GOVERNMENT SUPPORT

This invention was made with government support under grant numbers GM102864 awarded by the National Institutes of Health. The government has certain rights in the invention.

Throughout this application, certain publications are referenced in parentheses. Full citations for these publications may be found immediately preceding the claims. The disclosures of these publications in their entireties are hereby incorporated by reference into this application in order to describe more fully the state of the art to which this invention relates.

BACKGROUND OF THE INVENTION

Treatment of bacterial infections in humans is hindered by the relatively unsophisticated diagnostic methods that are currently available, some of which are either slow or inaccurate and often depend on the availability of clinical samples that contain bacteria. Positron emission tomography (PET) is a promising non-invasive imaging technique for detecting and localizing infection in humans. Most of the current studies rely on fludeoxyglucose (FDG), however this tracer lacks specificity since it is taken up by any cells that are using glucose including human cells involved in the inflammatory response to infection. Consequently, there is a need to develop sensitive and specific PET radiotracers for infection imaging.

2-Deoxy-2-[18F]fluoro-D-glucose ([$^{18}$F]FDG) is one of the most widely studied and used PET tracers. It is an analogue of glucose, and accumulates in tissues and organs that have high glycolytic activity such as tumor and brain cells. Therefore, FDG-PET is widely used in the detection and diagnosis of cancer and neurological disorders. FDG-PET has also been explored for the diagnosis of infection and indeed is used clinically for osteomyelitis, infective endocarditis, fever of unknown origin, tuberculosis and other infections. However, due to the fact that FDG accumulates in all cells with high glycolytic activity including inflammatory cells and tumor cells, the ability of FDG PET to correctly diagnose infection is limited, and results are often confounded by, for example, inflammation caused by other disorders as well as cancer.

Due to the lack of diagnostic sensitivity and specificity of FDG-PET, there have been several recent reports of novel infection tracers, including [$^{124}$I]FIAU (Bettegowda C. et al. 2005), a small molecule substrate for bacterial thymidine kinase, [$^{18}$F]fluorodeoxysorbitol (FDS) (Weinstein, E. A. et al. 2014; Li, Z. B. et al. 2008), and [$^{18}$F]-labeled maltose based small molecules (MH$^{18}$F and 6-[$^{18}$F]-fluoromaltose) (Namavari, M. et al. 2015; Gowrishankar, G. et al. 2014). However each tracer faces certain limitations for deployment as a *S. aureus* infection tracer, such as low signal-to-background ratio ([$^{124}$I]FIAU, 6-[$^{18}$F]-fluoromaltose), low radiochemical yield (MH$^{18}$F) or lack of uptake by *S. aureus* (FDS).

SUMMARY OF THE INVENTION

The present invention provides a composition comprising the compound having the structure:

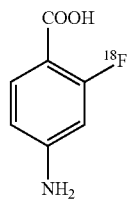 [SMILES: Nc1ccc(C(=O)O)c([18F])c1]

or a salt of the compound; 4-amino-2-[$^{19}$F]-fluorobenzoic acid or a salt of 4-amino-2-[$^{19}$F]-fluorobenzoic acid; and at least one acceptable carrier.

The present invention also provides a method of detecting the presence of an infectious bacteria in a subject which comprises determining if an amount of the compound having the structure:

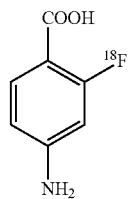

is present in the subject at a period of time after administration of the compound or salt thereof to the subject, thereby detecting the presence of the infectious bacteria based on the amount of the compound determined to be present in the subject.

The present invention further provides a method of detecting the location of bacteria cells in a subject afflicted with an infection of the bacteria which comprises determining where an amount of the compound having the structure:

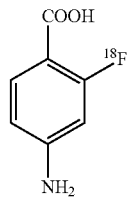

is present in the subject at a period of time after administration of the compound or salt thereof to the subject, thereby detecting the location of the bacteria cells based on the location of the compound determined to be present in the subject.

DETAILED DESCRIPTION OF THE INVENTION

Figure 1A:
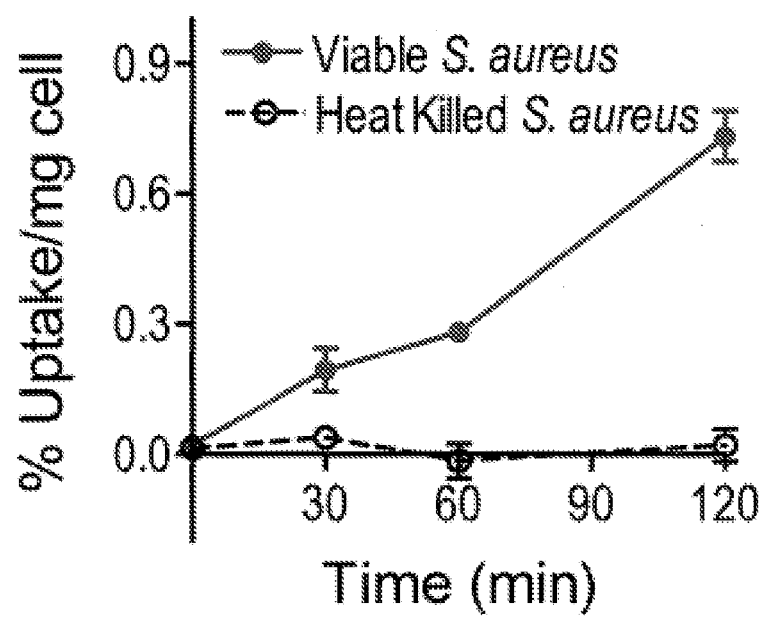
FIG. 1A: Percent uptake of [$^{18}$F]F-PABA by viable and heat-killed *S. Aureus*.

The present invention provides a composition comprising the compound having the structure:

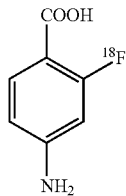

or a salt of the compound; 4-amino-2-[$^{19}$F]-fluorobenzoic acid or a salt of 4-amino-2-[$^{19}$F]-fluorobenzoic acid; and at least one acceptable carrier.

The present invention provides a composition comprising the compound having the structure:

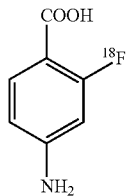

or a salt of the compound; and 4-amino-2-[$^{19}$F]-fluorobenzoic acid or a salt of 4-amino-2-[$^{19}$F]-fluorobenzoic acid.

In some embodiments, the ratio of the 4-amino-2-[$^{18}$F]-fluorobenzoic acid to the 4-amino-2-[$^{19}$F]-fluorobenzoic acid is in a range from 1:90 to 1:550.

In some embodiments, the ratio of the 4-amino-2-[$^{18}$F]-fluorobenzoic acid to the 4-amino-2-[$^{19}$F]-fluorobenzoic acid is in a range from 1:99 to 1:500.

In some embodiments, the ratio of the compound to the 4-amino-2-[$^{18}$F]-fluorobenzoic acid to the 4-amino-2-[$^{19}$F]-fluorobenzoic acid is in a range from 1:324 to 1:500.

In some embodiments, the ratio of the compound to the 4-amino-2-[$^{18}$F]-fluorobenzoic acid to the 4-amino-2-[$^{19}$F]-fluorobenzoic acid is in a range from 1:300 to 1:500.

In some embodiments, the ratio of the compound to the 4-amino-2-[$^{18}$F]-fluorobenzoic acid to the 4-amino-2-[$^{19}$F]-fluorobenzoic acid is in a range from 1:99 to 1:324.

In some embodiments, the ratio of the compound to the 4-amino-2-[$^{18}$F]-fluorobenzoic acid to the 4-amino-2-[$^{19}$F]-fluorobenzoic acid is in a range from 1:90 to 1:100.

In some embodiments, the ratio of the compound to the 4-amino-2-fluorobenzoic acid is about 1:99.

In some embodiments, the ratio of the compound to the 4-amino-2-fluorobenzoic acid is about 1:100.

In some embodiments, the ratio of the compound to the 4-amino-2-fluorobenzoic acid is about 1:134.

In some embodiments, the ratio of the compound to the 4-amino-2-fluorobenzoic acid is about 1:500.

In some embodiments, the radiochemical purity of 4-amino-2-[$^{18}$F]-fluorobenzoic acid is at least 90%.

In some embodiments, the radiochemical purity of 4-amino-2-[$^{18}$F]-fluorobenzoic acid is at least 93.5%.

In some embodiments, the radiochemical purity of 4-amino-2-[$^{18}$F]-fluorobenzoic acid is at least 95%

In some embodiments, the radiochemical purity of 4-amino-2-[$^{18}$F]-fluorobenzoic acid is at least 97.5%

In some embodiments, the radiochemical purity of 4-amino-2-[$^{18}$F]-fluorobenzoic acid is at least 99%.

In some embodiments, the composition further comprising 2-(fluoro-$^{18}$F)-4-nitrobenzoic acid or a salt of 2-(fluoro-$^{18}$F)-4-nitrobenzoic acid.

In some embodiments, the composition further comprising 4-amino-2-(fluoro-$^{18}$F)benzonitrile or a salt of 4-amino-2-(fluoro-$^{18}$F)benzonitrile.

The present invention provides a process for preparing the composition of the present invention comprising admixing at least one carrier with an amount of a compound having the structure:

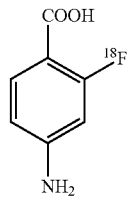 [SMILES: Nc1ccc(C(=O)O)c([18F])c1]

or a salt of the compound.

In some embodiments, a process for preparing the compound having the structure:

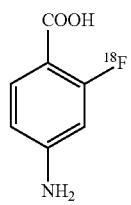 [SMILES: Nc1ccc(C(=O)O)c([18F])c1]

which comprises:

(a) reacting 2,4-dinitrobenzonitrile with a [$^{18}$F] fluorinating agent to obtain the compound having the structure:

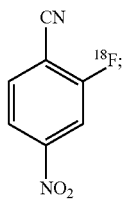

(b) hydrolyzing the nitrile group in the compound obtained in step (a) to obtain the compound having the structure:

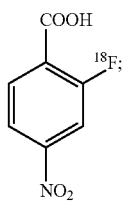

(c) reacting the compound obtained in step (b) with a reducing agent to obtain the compound having the structure:

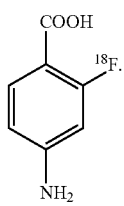

In some embodiments, a process for preparing the compound having the structure:

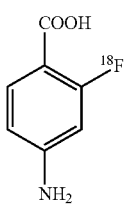

which comprises:

(a) reacting 2,4-dinitrobenzonitrile with a [$^{18}$F] fluorinating agent to obtain the compound having the structure:

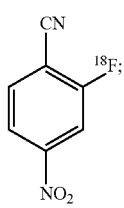

(b) reacting the compound obtained in step (a) with a reducing agent to obtain the compound having the structure:

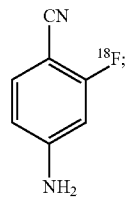

and (c) hydrolyzing the nitrile group in the compound obtained in step (b) to obtain the compound having the structure:

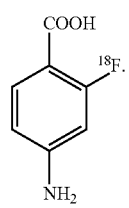

In some embodiments, the process wherein the [$^{18}$F] fluorinating agent is potassium [$^{18}$F] fluoride or tetra-n-butylammonium [$^{18}$F] fluoride.

In some embodiments, the process wherein step (a) further comprises a chelating agent.

In some embodiments, the process wherein the chelating agent is a crown ether.

In some embodiments, the process wherein the chelating agent is 4,7,13,16,21,24-Hexaoxa-1,10-diazabicyclo[8.8.8]hexacosane.

In some embodiments, the process wherein step (a) further comprises a base.

In some embodiments, the process wherein the base is potassium carbonate.

In some embodiments, the process wherein step (a) is performed at room temperature.

In some embodiments, the process wherein in step (b) the hydrolysis is facilitated by aqueous solution of a base.

In some embodiments, the process wherein the base is potassium hydroxide.

In some embodiments, the process wherein step (b) is performed at a temperature of 80-110° C.

In some embodiments, the process wherein step (b) is performed at a temperature of about 105° C.

In some embodiments, the process wherein in step (c) the hydrolysis is facilitated by aqueous solution of a base.

In some embodiments, the process wherein the base is potassium hydroxide.

In some embodiments, the process wherein step (c) is performed at a temperature of 80-110° C.

In some embodiments, the process wherein step (c) is performed at a temperature of about 105° C.

In some embodiments, the process wherein in step (c) the reducing agent is palladium-on-carbon, platinum (IV) oxide, nickel, nickel-aluminium alloy, spongy nickel, tin(II) chloride, titanium(III) chloride, iron metal or zinc metal.

In some embodiments, the process wherein in step (c) the reducing agent is zinc metal.

In some embodiments, the process wherein step (c) is performed at a temperature of 80-110° C.

In some embodiments, the process wherein step (c) is performed at a temperature of about 105° C.

In some embodiments, the process wherein steps (a) and (b) are conducted in the same pot; and step (c) is conducted in a separate pot.

In some embodiments, the process wherein in step (b) the reducing agent is palladium-on-carbon, platinum (IV) oxide, nickel, nickel-aluminum alloy, spongy nickel, tin(II) chloride, titanium(III) chloride, iron metal or zinc metal.

In some embodiments, the process wherein in step (b) the reducing agent is zinc metal.

In some embodiments, the process wherein step (b) is performed at a temperature of 80-110° C.

In some embodiments, the process wherein step (b) is performed at a temperature of about 105° C.

In some embodiments, the process wherein steps (a) and (b) are conducted in the same pot; and step (c) is conducted in a separate pot.

In some embodiments, a composition comprising the compound having the structure:

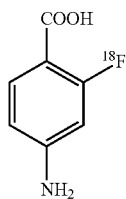

or a salt of the compound; 4-amino-2-[$^{19}$F]-fluorobenzoic acid or a salt of 4-amino-2-[$^{19}$F]-fluorobenzoic acid; and at least one acceptable carrier, wherein the compound is prepared by any of the processes disclosed above.

The present invention further provides a method of detecting the presence of an infectious bacteria in a subject which comprises determining if an amount of the compound having the structure:

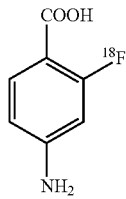

is present in the subject at a period of time after administration of the compound or salt thereof to the subject, thereby detecting the presence of the infectious bacteria based on the amount of the compound determined to be present in the subject.

The present invention further provides a method of detecting the location of bacteria cells in a subject afflicted with an infection of the bacteria which comprises determining where an amount of the compound having the structure:

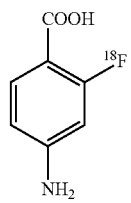 [SMILES: Nc1ccc(C(=O)O)c([18F])c1]

is present in the subject at a period of time after administration of the compound or salt thereof to the subject, thereby detecting the location of the bacteria cells based on the location of the compound determined to be present in the subject.

In some embodiments, the method further comprising quantifying the amount of the compound in the subject and comparing the quantity to a predetermined control.

In some embodiments, the method further comprising determining the level of infection in the subject based on the amount of the compound in the subject.

In some embodiments, the method wherein the determining is performed by a Positron Emission Tomography (PET) device.

In some embodiments, the method wherein the bacteria cells express dihydropteroate synthase (DHPS).

In some embodiments, the method wherein the subject is afflicted with a gram-negative bacterial infection other than *Enterococcus faecalis*.

In some embodiments, the method wherein the subject is afflicted with a gram-positive bacterial infection In some embodiments, the method wherein the subject is afflicted with a *Mycobacterium tuberculosis* bacterial infection.

In some embodiments, the method wherein the subject is afflicted with a Methicillin-sensitive *Staphylococcus aureus* bacterial infection.

In some embodiments, the method wherein the subject is afflicted with a Methicillin-resistant *Staphylococcus aureus* bacterial infection.

In some embodiments, the method further comprising subjecting the subject to antibiotic treatment when the presence of an infectious bacteria or the location of bacteria cells is detected.

In some embodiments, the method wherein the antibiotic is a penicillin, a cephalosporin, a macrolide, a fluoroquinolone, a tetracycline, a carbapenem or an aminoglycoside antibiotic.

In some embodiments, a method of imaging bacteria cells of in a subject afflicted with an infection of the bacteria which comprises:

(i) administering to the subject a composition comprising the compound having the structure:

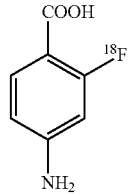

or a salt of the compound, and at least one acceptable carrier;
(ii) imaging at least a portion of the subject;
(iii) detecting in the subject the location of the compound, thereby determining the location of the bacteria cells present in the subject based on the location of the compound in the subject; and
(v) obtaining an image of the location of the bacteria cells.

In some embodiments, the above method further comprising:
(vii) repeating steps (v)-(vii) one or more times.

In some embodiments, a method of determining the location of bacteria cells of in a subject afflicted with an infection of the bacteria which comprises:
(i) administering to the subject a composition comprising the compound having the structure:

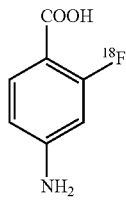

or a salt of the compound, and at least one acceptable carrier;
(ii) allowing a sufficient period of time for bacteria cells in the subject to take up the compound;
(iii) imaging at least a portion of the subject; and
(iv) detecting in the subject the location of the compound, thereby determining the location of the bacteria cells present in the subject based on the location of the compound in the subject.

In some embodiments of any of the disclosed methods, the compound accumulates in the cells of the bacteria.

In some embodiments of any of the disclosed methods, the compound accumulates in the cells of the bacteria by incorporation into the folate biosynthesis pathway of the bacteria.

4-Amino-2-[$^{18}$f]-fluorobenzoic acid ([$^{18}$F]F-PABA) has the following structure:

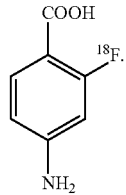

The present invention also provides a composition comprising [$^{18}$F]F-PABA.

The present invention also provides a composition comprising [$^{18}$F]F-PABA and a pharmaceutically acceptable carrier.

In some embodiments, a method for the detection of bacteria cells in a subject comprising:
(i) administering to the subject an effective amount of the composition of the present invention;
(ii) allowing a sufficient period of time for the bacteria cells to take up the [$^{18}$F]F-PABA in the composition; and (iii) determining whether the bacteria cells are present in the host by detecting the [$^{18}$F]F-PABA the subject.

In some embodiments, a method of imaging bacteria cells of in a subject afflicted with an infection of the bacteria which comprises:
(i) administering to the subject an effective amount of the composition of the present invention;
(ii) imaging at least a portion of the subject;
(iii) detecting in the subject the location of the [$^{18}$F]F-PABA, thereby determining the location of the bacteria cells present in the subject based on the location of the [$^{18}$F]F-PABA in the subject;
(v) obtaining an image of the location of the bacteria cells; and optionally the following step:
(vi) repeating steps (i)-(v) one or more times.

In some embodiments, a method of determining the location of bacteria cells of in a subject afflicted with an infection of the bacteria which comprises:
(i) administering to the subject an effective amount of the composition of the present invention;
(ii) allowing a sufficient period of time for bacteria cells in the subject to take up the [$^{18}$F]F-PABA;
(iii) imaging at least a portion of the subject; and
(iv) detecting in the subject the location of the [$^{18}$F]F-PABA, thereby determining the location of the bacteria cells present in the subject based on the location of the [$^{18}$F]F-PABA in the subject.

In some embodiments of any of the disclosed methods, the bacteria lacks a folate salvage pathway.

In some embodiments of any of the disclosed methods, the bacteria is methicillin sensitive *S. aureus* (MSSA), methicillin-resistant *S. aureus* (MRSA), Gram negative bacteria *E. coli* or Gram negative bacteria *Klebsiela pneumoniae* or *Mycobacterium tuberculosis*.

In some embodiments of any of the disclosed methods, the [$^{18}$F]F-PABA accumulates in the cells of the bacteria by incorporation into the folate biosynthesis pathway.

In some embodiments of any of the disclosed methods, the [$^{18}$F]F-PABA is a substrate for DHPS.

In some embodiments of any of the disclosed methods, DHPS catalyses the condensation of 6-hydroxymethyl-7,8-dihydropteridine pyrophosphate to the [($^{18}$F]F-PABA to form 4-(((2-amino-4-oxo-3,4-dihydropteridin-6-yl)methyl)amino)-2-[$^{18}$F]fluorobenzoic acid.

In some embodiments, the infectious bacteria is Gram-negative bacteria or Gram-positive bacteria.

In some embodiments, the infectious bacteria is *Mycobacterium tuberculosis*.

In some embodiments, the Gram-negative bacteria infection is drug-resistant or multi-drug resistant.

In some embodiments, the Gram-positive bacteria infection is drug-resistant or multi-drug resistant.

In some embodiments, the *Mycobacterium tuberculosis* infection is drug-resistant or multi-drug resistant.

In some embodiments, the Gram-negative bacteria cells are drug-resistant or multi-drug resistant.

In some embodiments, the Gram-positive bacteria cells are drug-resistant or multi-drug resistant.

In some embodiments, the method wherein the *Mycobacterium tuberculosis* cells are drug-resistant or multi-drug resistant.

In some embodiments, the Gram-negative bacteria is *Escherichia coli, Klebsiella pneunomiae, Burkholderia cepacia, Pseudomonas aeruginosa* or *Acinetobacter baumanii*.

In some embodiments, the Gram-negative bacteria is other than *Enterococcus faecalis*.

In some embodiments, the Gram-positive bacteria is *Enterococcus faecalis, Enterococcus faecium, Staphylococcus aureus, Staphylococcus epidermidis, Staphylococcus haemolyticus, Staphylococcus lugdunensis, Staphylococcus saprophyticus, Staphylococcus hominis, Staphylococcus capitis, Streptococcus intermedius Streptococcus anginosus, Streptococcus constellatus, Streptococcus pneumoniae, Streptobacillus moniliformis, Streptococcus pyogenes, Streptococcus agalactiae, Actinomyces israelii, Arcanobacterium haemolyticum, Bacillus anthracis, Bacillus cereus, Bacillus subtilis, Clostridium difficile, Clostridium perfringens, Clostridium tetani, Corynebacterium diphtheria, Corynebacterium jeikeium, Corynebacterium urealyticum, Erysipelothrix rhusiopathiae, Listeria monocytogenes, Nocardia asteroides, Nocardia brasiliensis, Propionibacterium acnes* or *Rhodococcus equi*.

In one embodiment, wherein the antibiotic includes, but is not limited to, fluoroquinolines, tetracyclines, macrolides, glycopeptides, sulfonamides, aminoglycosides, cephalosporins and/or penicillins.

In one embodiment, wherein the antibiotic is selected from the group consisting of ampicillin, piperacillin, penicillin G, ticarcillin, imipenem, meropenem, azithromycin, erythromycin, aztreonam, cefepime, cefotaxime, ceftriaxone, ceftazidime, ciprofloxacin, levofloxacin, clindamycin, doxycycline, gentamycin, amikacin, tobramycin, tetracycline, tigecycline, rifampicin, vancomycin and polymyxin.

In one embodiment, wherein the antibiotic is selected from the group consisting of gentamicin, amikacin, tobramycin, ciprofloxacin, levofloxacin, ceftazidime, cefepime, cefoperazone, cefpirome, ceftobiprole, carbenicillin, ticarcillin, mezlocillin, azlocillin, piperacillin, meropenem, imipenem, doripenem, polymyxin B, colistin and aztreonam.

In one embodiment, the subject is afflicted with osteomyelitis or or enocarditis.

In one embodiment, the subject is afflicted with diabetes.

In one embodiment, a process for manufacturing a composition which comprises obtaining the compound having the structure:

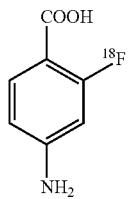

and combining the compound with a carrier so as to thereby manufacture the composition.

In one embodiment, a process for manufacturing a composition which comprises obtaining the compound having the structure:

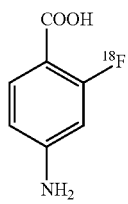

by any one of the processes disclosed herein and combining the compound with a carrier so as to thereby manufacture the composition.

As used herein, a "symptom" associated with a disease or disorder includes any clinical or laboratory manifestation associated with the disease or disorder and is not limited to what the subject can feel or observe.

As used herein, "treating", e.g. of an infection, encompasses inducing prevention, inhibition, regression, or stasis of the disease or a symptom or condition associated with the infection.

The compounds of the present invention include all hydrates, solvates, and complexes of the compounds used by this invention. If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. The compounds described in the present invention are in racemic form or as individual enantiomers. The enantiomers can be separated using known techniques, such as those described in Pure and Applied Chemistry 69, 1469-1474, (1997) IUPAC. In cases in which compounds have unsaturated carbon-carbon double bonds, both the cis (Z) and trans (E) isomers are within the scope of this invention.

The compounds of the subject invention may have spontaneous tautomeric forms. In cases wherein compounds may exist in tautomeric forms, such as keto-enol tautomers, each tautomeric form is contemplated as being included within this invention whether existing in equilibrium or predominantly in one form.

In the compound structures depicted herein, hydrogen atoms are not shown for carbon atoms having less than four bonds to non-hydrogen atoms. However, it is understood that enough hydrogen atoms exist on said carbon atoms to satisfy the octet rule.

This invention also provides isotopic variants of the compounds disclosed herein, including wherein the isotopic atom is $^2H$ and/or wherein the isotopic atom $^{13}C$. Accordingly, in the compounds provided herein hydrogen can be enriched in the deuterium isotope. It is to be understood that the invention encompasses all such isotopic forms.

It is understood that the structures described in the embodiments of the methods hereinabove can be the same as the structures of the compounds described hereinabove.

It is understood that where a numerical range is recited herein, the present invention contemplates each integer between, and including, the upper and lower limits, unless otherwise stated.

Except where otherwise specified, if the structure of a compound of this invention includes an asymmetric carbon atom, it is understood that the compound occurs as a racemate, racemic mixture, and isolated single enantiomer. All such isomeric forms of these compounds are expressly included in this invention. Except where otherwise specified, each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "Enantiomers, Racemates and Resolutions" by J. Jacques, A. Collet and S. Wilen, Pub. John Wiley & Sons, N Y, 1981. For example, the resolution may be carried out by preparative chromatography on a chiral column.

The subject invention is also intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include C-13 and C-14.

It will be noted that any notation of a carbon in structures throughout this application, when used without further notation, are intended to represent all isotopes of carbon, such as $^{12}C$, $^{13}C$, or $^{14}C$. Furthermore, any compounds containing $^{13}C$ or $^{14}C$ may specifically have the structure of any of the compounds disclosed herein.

It will also be noted that any notation of a hydrogen in structures throughout this application, when used without further notation, are intended to represent all isotopes of hydrogen, such as $^{1}H$, $^{2}H$, or $^{3}H$. Furthermore, any compounds containing $^{2}H$ or $^{3}H$ may specifically have the structure of any of the compounds disclosed herein.

Isotopically-labeled compounds can generally be prepared by conventional techniques known to those skilled in the art using appropriate isotopically-labeled reagents in place of the non-labeled reagents employed.

In the compounds used in the method of the present invention, the substituents may be substituted or unsubstituted, unless specifically defined otherwise.

It is understood that substituents and substitution patterns on the compounds used in the method of the present invention can be selected by one of ordinary skill in the art to provide compounds that are chemically stable and that can be readily synthesized by techniques known in the art from readily available starting materials. If a substituent is itself substituted with more than one group, it is understood that these multiple groups may be on the same carbon or on different carbons, so long as a stable structure results.

In choosing the compounds used in the method of the present invention, one of ordinary skill in the art will recognize that the various substituents, i.e. $R_1$, $R_2$, etc. are to be chosen in conformity with well-known principles of chemical structure connectivity.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

In choosing the compounds of the present invention, one of ordinary skill in the art will recognize that the various substituents, i.e. $R_1$, $R_2$, etc. are to be chosen in conformity with well-known principles of chemical structure connectivity.

The various R groups attached to the aromatic rings of the compounds disclosed herein may be added to the rings by standard procedures, for example those set forth in Advanced Organic Chemistry: Part B: Reaction and Synthesis, Francis Carey and Richard Sundberg, (Springer) 5th ed. Edition. (2007), the content of which is hereby incorporated by reference.

The compounds used in the method of the present invention may be prepared by techniques well known in organic synthesis and familiar to a practitioner ordinarily skilled in the art. However, these may not be the only means by which to synthesize or obtain the desired compounds.

The compounds used in the method of the present invention may be prepared by techniques described in Vogel's Textbook of Practical Organic Chemistry, A. I. Vogel, A. R. Tatchell, B. S. Furnis, A. J. Hannaford, P. W. G. Smith, (Prentice Hall) $5^{th}$ Edition (1996), March's Advanced Organic Chemistry: Reactions, Mechanisms, and Structure, Michael B. Smith, Jerry March, (Wiley-Interscience) $5^{th}$ Edition (2007), and references therein, which are incorporated by reference herein. However, these may not be the only means by which to synthesize or obtain the desired compounds.

Another aspect of the invention comprises a compound used in the method of the present invention as a pharmaceutical composition.

In some embodiments, a pharmaceutical composition comprising the compound of the present invention and a pharmaceutically acceptable carrier.

As used herein, the term "pharmaceutically active agent" means any substance or compound suitable for administration to a subject and furnishes biological activity or other direct effect in the treatment, cure, mitigation, diagnosis, or prevention of disease, or affects the structure or any function of the subject. Pharmaceutically active agents include, but are not limited to, substances and compounds described in the Physicians' Desk Reference (PDR Network, LLC; 64th edition; Nov. 15, 2009) and "Approved Drug Products with Therapeutic Equivalence Evaluations" (U.S. Department Of Health And Human Services, $30^{th}$ edition, 2010), which are hereby incorporated by reference. Pharmaceutically active agents which have pendant carboxylic acid groups may be modified in accordance with the present invention using standard esterification reactions and methods readily available and known to those having ordinary skill in the art of chemical synthesis. Where a pharmaceutically active agent does not possess a carboxylic acid group, the ordinarily skilled artisan will be able to design and incorporate a carboxylic acid group into the pharmaceutically active agent where esterification may subsequently be carried out so long as the modification does not interfere with the pharmaceutically active agent's biological activity or effect.

The compounds used in the method of the present invention may be in a salt form. As used herein, a "salt" is a salt of the instant compounds which has been modified by making acid or base salts of the compounds. In the case of compounds used to treat an infection or disease caused by a pathogen, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkali earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like. (See, e.g., Berge et al. (1977) "Pharmaceutical Salts", *J. Pharm. Sci.* 66:1-19).

The compounds of the present invention may also form salts with basic amino acids such a lysine, arginine, etc. and with basic sugars such as N-methylglucamine, 2-amino-2-deoxyglucose, etc. and any other physiologically non-toxic basic substance.

As used herein, "administering" an agent may be performed using any of the various methods or delivery systems well known to those skilled in the art. The administering can be performed, for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery, subcutaneously, intraadiposally, intraarticularly, intrathecally, into a cerebral ventricle, intraventicularly, intratumorally, into cerebral parenchyma or intraparenchchymally.

The compounds used in the method of the present invention may be administered in various forms, including those detailed herein. The treatment with the compound may be a component of a combination therapy or an adjunct therapy, i.e. the subject or patient in need of the drug is treated or given another drug for the disease in conjunction with one or more of the instant compounds. This combination therapy can be sequential therapy where the patient is treated first with one drug and then the other or the two drugs are given simultaneously. These can be administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compounds to the animal or human. The carrier may be liquid or solid and is selected with the planned manner of administration in mind. Liposomes are also a pharmaceutically acceptable carrier as are slow-release vehicles.

The dosage of the compounds administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds used in the method of the present invention may comprise a single compound or mixtures thereof with additional antitumor agents. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection, topical application, or other methods, into or topically onto a site of disease or lesion, all using dosage forms well known to those of ordinary skill in the pharmaceutical arts.

The compounds used in the method of the present invention can be administered in admixture with suitable pharmaceutical diluents, extenders, excipients, or in carriers such as the novel programmable sustained-release multi-compartmental nanospheres (collectively referred to herein as a pharmaceutically acceptable carrier) suitably selected with respect to the intended form of administration and as consistent with conventional pharmaceutical practices. The unit will be in a form suitable for oral, nasal, rectal, topical, intravenous or direct injection or parenteral administration. The compounds can be administered alone or mixed with a pharmaceutically acceptable carrier. This carrier can be a solid or liquid, and the type of carrier is generally chosen based on the type of administration being used. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds used in the method of the present invention may also be administered in the form of liposome delivery systems, such as small unilamellar vesicles, large unilamellar vesicles, and multilamellar vesicles. Liposomes can be formed from a variety of phospholipids such as lecithin, sphingomyelin, proteolipids, protein-encapsulated vesicles or from cholesterol, stearylamine, or phosphatidylcholines. The compounds may be administered as components of tissue-targeted emulsions.

The compounds used in the method of the present invention may also be coupled to soluble polymers as targetable drug carriers or as a prodrug. Such polymers include polyvinylpyrrolidone, pyran copolymer, polyhydroxylpropylmethacrylamide-phenol, polyhydroxyethylaspartamidephenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient compounds and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar-coated or film-coated to mask any unpleasant taste and protect the tablet from the atmosphere, or enteric coated for selective disintegration in the gastrointestinal tract.

For oral administration in liquid dosage form, the oral drug components are combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, asuitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

The compounds used in the method of the present invention may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials such as solutol and/or ethanol to make them compatible with the type of injection or delivery system chosen.

The compounds and compositions of the present invention can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by topical administration, injection or other methods, to the afflicted area, such as a wound, including ulcers of the skin, all using dosage forms well known to those of ordinary skill in the pharmaceutical arts.

Specific examples of pharmaceutically acceptable carriers and excipients that may be used to formulate oral dosage forms of the present invention are described in U.S. Pat. No. 3,903,297 to Robert, issued Sep. 2, 1975. Techniques and compositions for making dosage forms useful in the present invention are described-in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

The active ingredient can be administered orally in solid dosage forms, such as capsules, tablets, powders, and chewing gum; or in liquid dosage forms, such as elixirs, syrups, and suspensions, including, but not limited to, mouthwash and toothpaste. It can also be administered parentally, in sterile liquid dosage forms.

Solid dosage forms, such as capsules and tablets, may be enteric-coated to prevent release of the active ingredient compounds before they reach the small intestine. Materials that may be used as enteric coatings include, but are not limited to, sugars, fatty acids, proteinaceous substances such as gelatin, waxes, shellac, cellulose acetate phthalate (CAP), methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), and methyl methacrylate-methacrylic acid copolymers.

The compounds and compositions of the invention can be coated onto stents for temporary or permanent implantation into the cardiovascular system of a subject.

Variations on those general synthetic methods will be readily apparent to those of ordinary skill in the art and are deemed to be within the scope of the present invention.

Each embodiment disclosed herein is contemplated as being applicable to each of the other disclosed embodiments. Thus, all combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Example 1. Synthesis of [$^{18}$F]F-PABA 2,4-Finitrobenzonitrile is used as the starting material. The ortho-nitro group is replaced by $^{18}$F through a nucleophilic aromatic substitution reaction followed by oxidation of the nitrile group to a carboxylic acid and then reduction of the p-nitro group to an amine (Scheme 1). The radiosynthesis including purification and formulation is accomplished in 120 min with a typical decay-corrected yield of 37.0% and radiochemical purity of ~97.5%. Typical specific activity of the final tracer is 19 mCi/μg, which may range from ~5 mCi of tracer. In a GMP facility 100 mCi of [$^{18}$F]F-PABA may be produced.

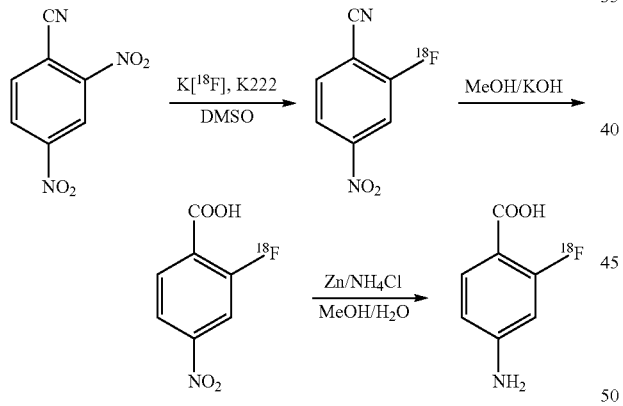

Scheme 1. General [$^{18}$F] F-PABA Synthesis.

Three-Step Synthesis (See Scheme 2)

Step 1

[$^{18}$F]Fluoride dissolved in ddH$_2$O was transferred to a reaction vial containing Kryptofix 2.2.2 (8 mg) and potassium carbonate (1 mg). The solution was dried by azeotropic distillation by adding acetonitrile portion wise. The solid residue was re-solubilized with 0.2-0.3 ml of DMSO containing a required amount of the precursor 2, 4-dinitrobenzonitrile (compound 1, 2 mg). The reaction mixture was stirred in the sealed vial for 10 min at RT. The color of the reaction mixture changed from yellow to maroon. The reaction mixture was then diluted with 10 ml H2O and run through a Waters Oasis plus HLB followed by a Waters C18 Sep-pak. The loading procedure was carried out by air pushing or vacuum drawing with a flow rate around 0.8 mL/min. The air that drives the solvent through the cartridges was kept running for another minute after the elution procedure to ensure all solvent was pushed out. The two cartridges were then eluted with 3 ml MeOH. The MeOH solution was directed back into the original reactor and was dried under vacuum.

Step 2

1 ml 2M KOH solution was added to the dried reaction vial. The reaction mixture was heated to 105° C. and stirred for 10 min. The reaction was quenched by 2 ml 2M acetic acid solution and additional 5 ml H$_2$O. The reaction mixture was run through another Waters Oasis plus HlB followed by a Waters C18 Sep-pak. It was then eluted with 2×1.2 ml MeCN into the second reactor which contained 10 mg Zn and 45 mg NH4CI. MeCN was dried under vacuum.

Step 3

1 ml H$_2$O was added to dried reaction vial 2. The reaction mixture was heated to 105° C. and stirred for 5 min in presence of 10 mg zinc powder and ~45 mg ammonium chloride. The product was then filtered through a venting 0.22 um filter and the reactor/filter washed with 4 ml of water. This mixture was then loaded onto 250×10 mm C18 column and eluted with 5% ethanol, 0.5% acetic acid at 4 ml/min. Purified [$^{18}$F]F-PABA elutes at around 18 minutes.

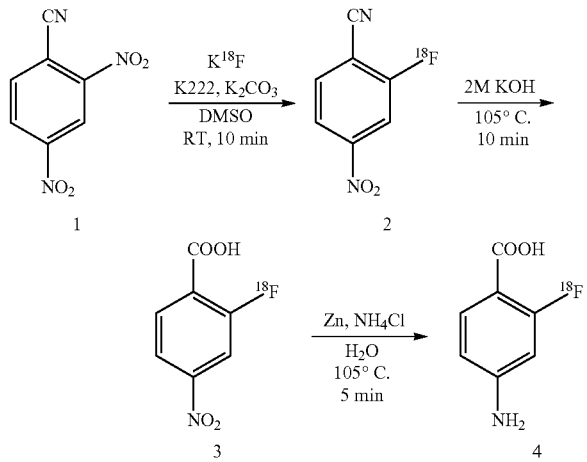

Scheme 2. Detailed [$^{18}$F] F-PABA Synthesis.

[$^{18}$F]FPABA can be conveniently prepared with a commercial remote chemistry units, such as the GE Tracerlab FXN pro. The FXN chemistry unit is reconfigured such that reservoirs 7 and 8 are connected with a cross piece to the line running between reservoir 6 and valve VX4.

For the synthesis, [$^{18}$F] fluoride is trapped on a Waters Sep-Pak light Accell plus QMA cartridge. The [$^{18}$F] fluoride is then eluted with 1 mL of potassium carbonate (4 mg/mL)/Kryptofix® [2.2.2] (14.4 mg/mL) in 96% acetonitrile into the reaction vessel. This solution is evaporated to dryness under a stream of nitrogen before being heated to 100° C. for one minute. The reaction vial is cooled to 40° C. and 2.0 mg of 2,4-dinitrobenzonitrile in 1 mL DMSO added. The reaction vessel is sealed and stirred for 6 minutes. The mixture is then diluted with 8 mL of water before being loaded onto conditioned an Oasis HLB and Sep-Pal light C18 cartridges in series. The cartridges are then back flushed with 3 mL acetonitrile to elute the desired 2-[$^{18}$F] fluoro-4-nitrobenzonitrile which is returned to the original reaction vessel. The cartridges are eluted with 8 mL of water so that they can be reused after the second reaction. The acetonitrile is removed under a stream of nitrogen gas at 40° C. for 3 minutes. One milliliter of 2 M potassium hydroxide is added to the residue. The reaction vessel is sealed and heated to 105° C. for 10 minutes. The reaction vessel is then cooled to 40° C. before 2 mL of 2M acetic acid and 5 mL of water are added. The mixture is stirred before being passed over previously used HLB and C18 cartridges. The cartridges are then back flushed with 1.5 ml acetonitrile to elute 2-[$^{18}$F] fluoro-4-nitrobenzoic acid to a second reaction vessel containing 10 mg of zinc powder. The acetonitrile is removed under a stream of nitrogen at 60° C. Sixty milligrams of ammonium chloride in 1 mL of water and 0.1 mL of 2M acetic acid are then added to the second reaction vessel. The reaction vessel is then sealed and heated up to 105° C. for five minutes. The reaction vessel is cooled and the contents flushed through a 0.22 μm filter using 4.5 mL of water. This filtered solution is mixed and purified with HPLC (Phenomenex Luna 10 μm $C_{18}$(2)100 Å, 250×10 mm) using an eluent of 0.5% acetic acid/5% ethanol at a flow rate of 5 mL/min. The desired product, 4-amino-2-[$^{18}$F] fluorobenzoic acid elutes at 18 minutes.

The overall synthesis time is 85 minutes, with a mean decay corrected yield of 30% (n=6). Starting with 400-1000 mCi of 18F, the mean specific activities of [$^{18}$F]F-PABA is 34 mCi/μg. The mean radiochemical purity is 99.1%.

Example 2. F-PABA is a Substrate for DHPS and is not Toxic to Either Bacterial or Mammalian Cells Expressed and purified dihydropteroate synthase (DHPS) from *S. aureus* (saDHPS) was cloned. DHPS is the enzyme that installs PABA (p-aminobenzoic acid) in the folate biosynthesis pathway (Scheme 2). It has been demonstrated that the PABA analog PAS (2-aminosalicylate) is incorporated into folic acid in *M. tuberculosis* (Chakraborty, S. et al. 2013), suggesting that PAS is a substrate for DHPS. Using a coupled assay, it was determined that the kinetic parameters for saDHPS with PABA, PAS and F-PABA. Importantly, all three compounds have similar kcat and Km values indicating that F-PABA is an alternative substrate for saDHPS. Since PAS is an antibacterial compound whose mechanism of action may be related for the ability of this compound to compete with PABA for DHPS, we determined the antibacterial activity and cytotoxicity of F-PABA for several bacterial species as well as Vero cells. In each case no growth inhibition was observed up to 200 μg/ml. Unlike PAA, 2-F-PABA has no antibacterial activity (Table 1).

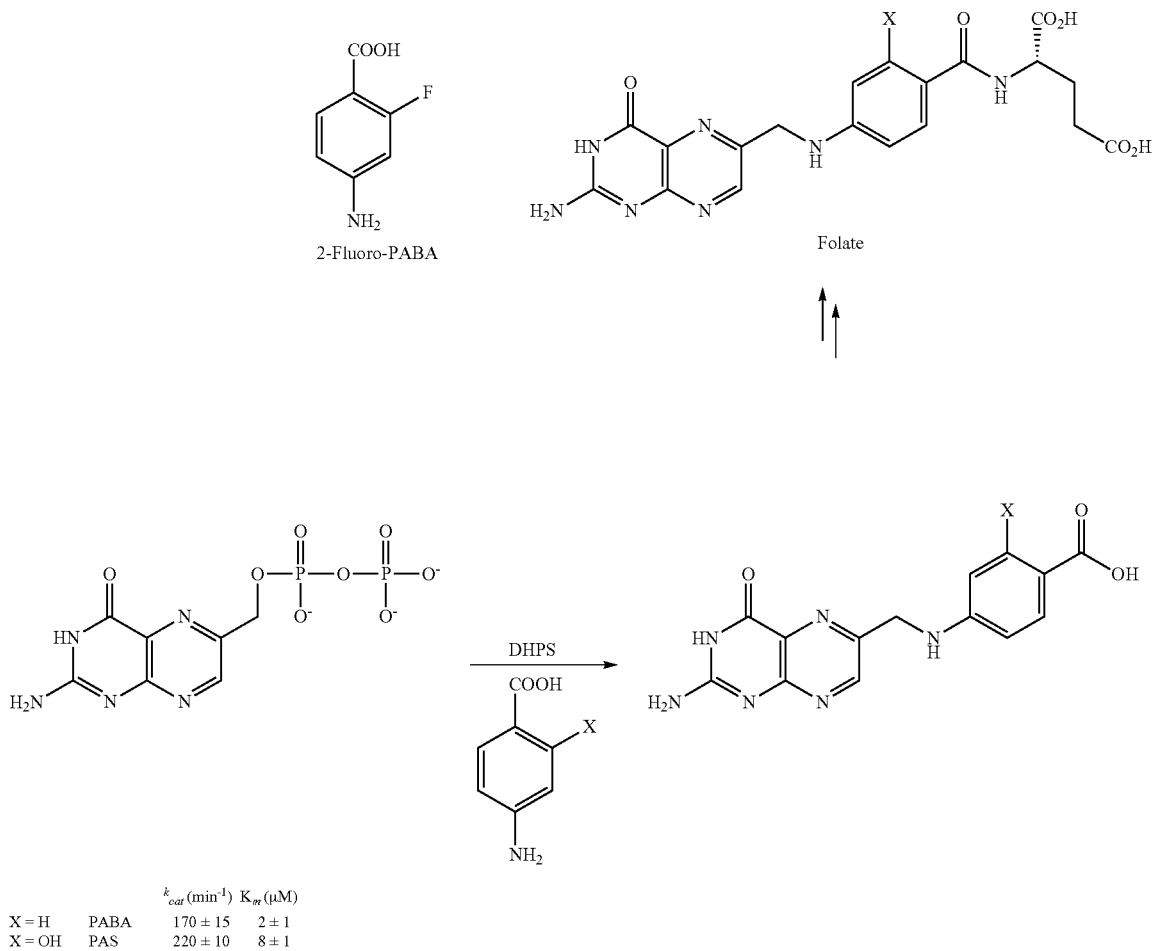

Scheme 2. PABA, PAS and F-PABA are substrates for DHPS in the tetrahydrofolate (THF) biosynthesis pathway.

|   |   | $k_{cat}$(min$^{-1}$) | K$_m$ (μM) |
|---|---|---|---|
| X = H | PABA | 170 ± 15 | 2 ± 1 |
| X = OH | PAS | 220 ± 10 | 8 ± 1 |
| X = F | F-PABA | 200 ± 20 | 5 ± 2 |

TABLE 1

| | MIC (μg/ml) | |
| --- | --- | --- |
| | 2-F-PABA | PAS |
| M. tuberculosis | >100 | 0.08 |
| S. aureus | >200 | >200 |
| E. coli | >200 | >200 |

Example 3. [$^{18}$F]F-PABA is Taken Up by S. aureus, E. Coli and K. pneumoniae, but not by E. faecalis The ability of different bacterial species to take up [$^{18}$F] F-PABA was studied. The radiotracer accumulated in both methicillin sensitive S. aureus (MSSA, Newman) and methicillin-resistant S. aureus (MRSA), as well as the Gram negative bacteria E. coli and Klebsiela pneumoniae.

Figure 1B:
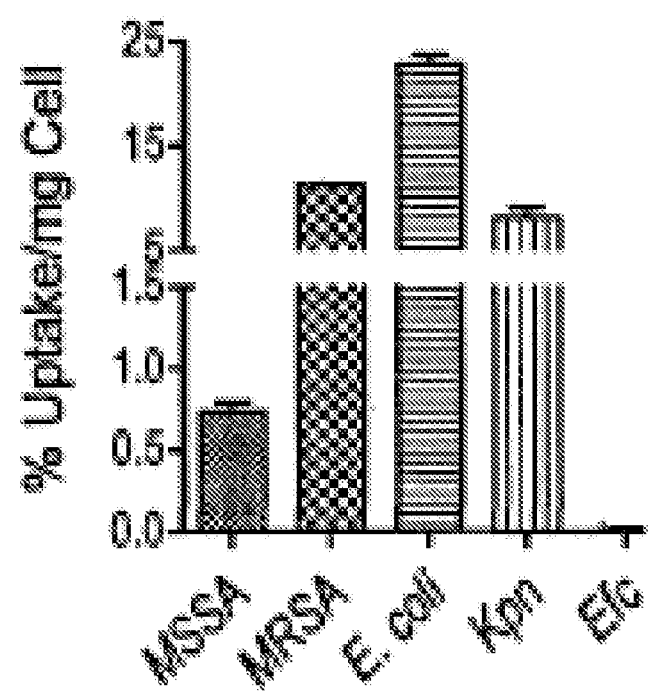
FIG. 1B: Percent uptake of [$^{18}$F]F-PABA by MSSA, MSRA, E. coli, K. pneumoniae and E. faecalis.

In the case of MSSA we also demonstrated that heat-killed cells were unable to take up [$^{18}$F]F-PABA (FIG. 1). In contrast, [$^{18}$F]F-PABA was not taken up by Enterococcus faecalis. E. faecalis has a folate salvage pathway and can take up folate from the environment. Thus, folic acid biosynthesis is dispensable in this organism, which also explains why sulfonamides are not used to treat infection by E. faecalis. These studies suggest that F-PABA uptake depends on on the de novo biosynthesis of folate.

Figure 2A:
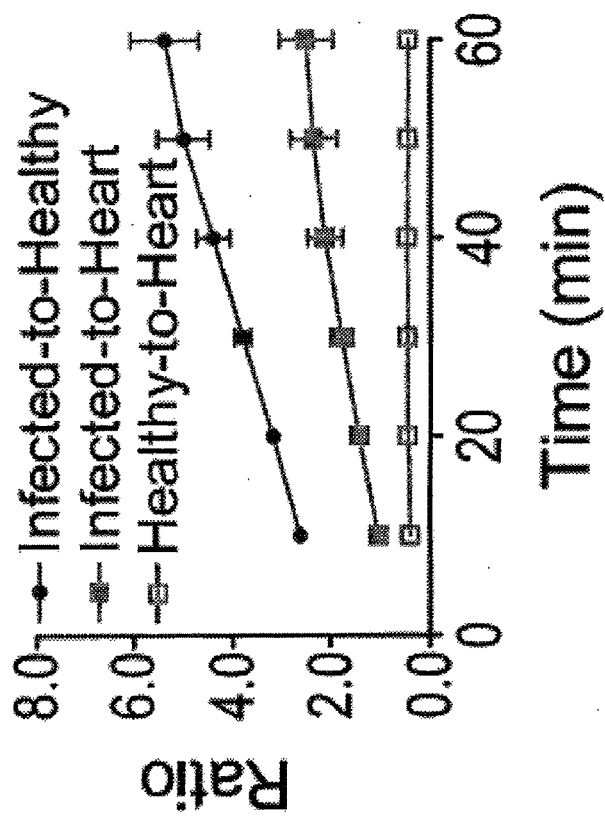
FIG. 2A: Imaging of [$^{18}$F]F-PABA in the triceps of an infected rat (right triceps infected with S. aureus).
Figure 2A:
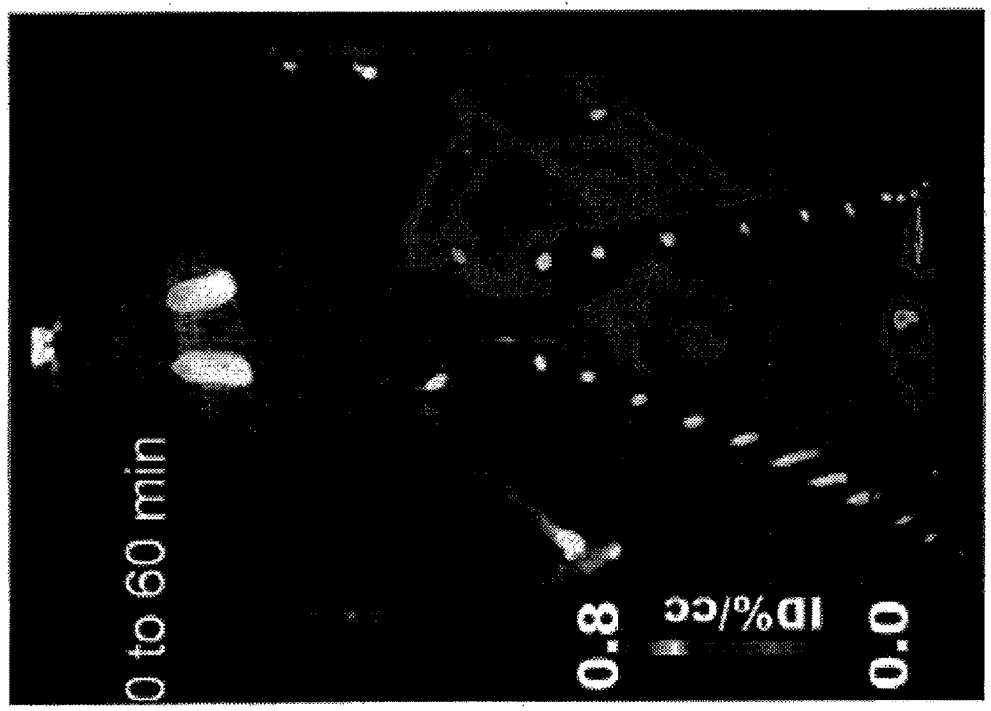
Figure 2B:
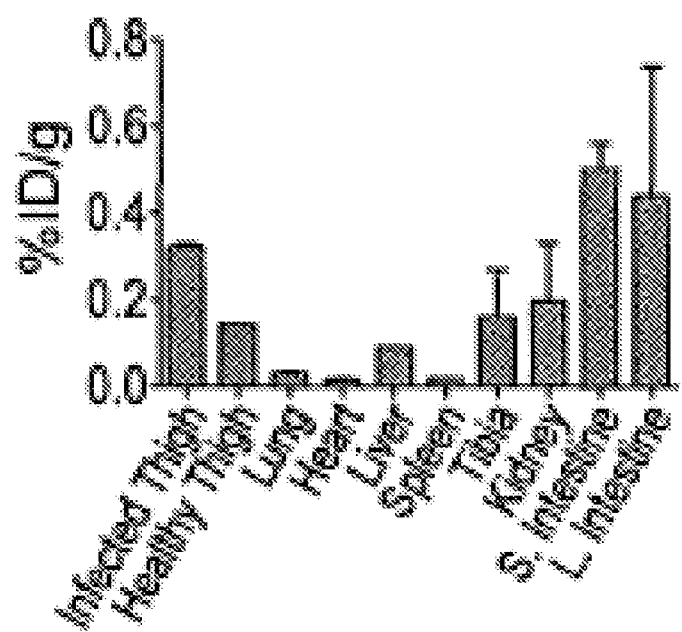
FIG. 2B: Tracer accumulation at different tissues and organs of an infected rat following iv administration of [$^{18}$F]F-PABA.

Example 4. [$^{18}$F]F-PABA Accumulates at the Site of S. aureus Infection in Rat Triceps and Mouse Thigh Infection Models Initial in vivo studies focused on soft tissue models of MSSA infection. This included a mouse thigh infection model and rat triceps model. FIG. 2 shows data for the accumulation of [$^{18}$F]F-PABA in the triceps of an infected rat. Fifty μL of 10$^9$ CFU of Newman S. aureus BHI culture was injected into the right triceps of a rat. After 10-15 hr the rats were imaged following iv administration of 0.8-1.2 mCi of [$^{18}$F]F-PABA. The images clearly show the accumulation of radioactivity in the right but not the left triceps. In addition to monitoring the time course of [$^{18}$F]F-PABA biodistribution, we also quantified tracer levels by postmortem ex vivo counting. While the [$^{18}$F]F-PABA distributed to all tissues and organs with the exception of the brain, significant tracer accumulation was only observed in the right triceps, as well as the kidney, bladder and GI tracts due to tracer clearance. At 60 min tracer levels were 5.4× higher in the infected right triceps compared to the uninfected left triceps. This compares favorably with other tracers.

Figure 3A:
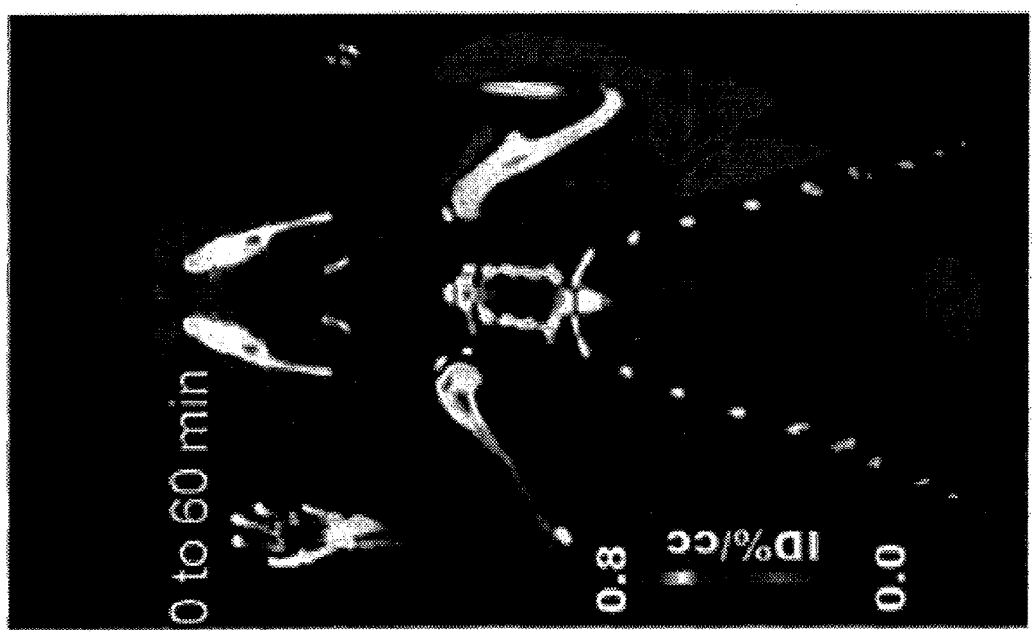
FIG. 3A: Imaging of [$^{18}$F]F-PABA in the triceps of an infected rat (right triceps—infected with S. aureus; left triceps—inflammation induced by heat killed S. aureus).
Figure 3A:
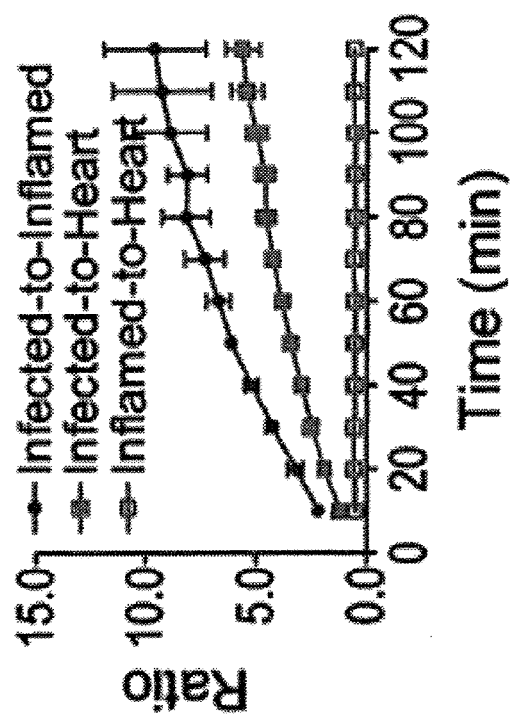
Figure 3B:
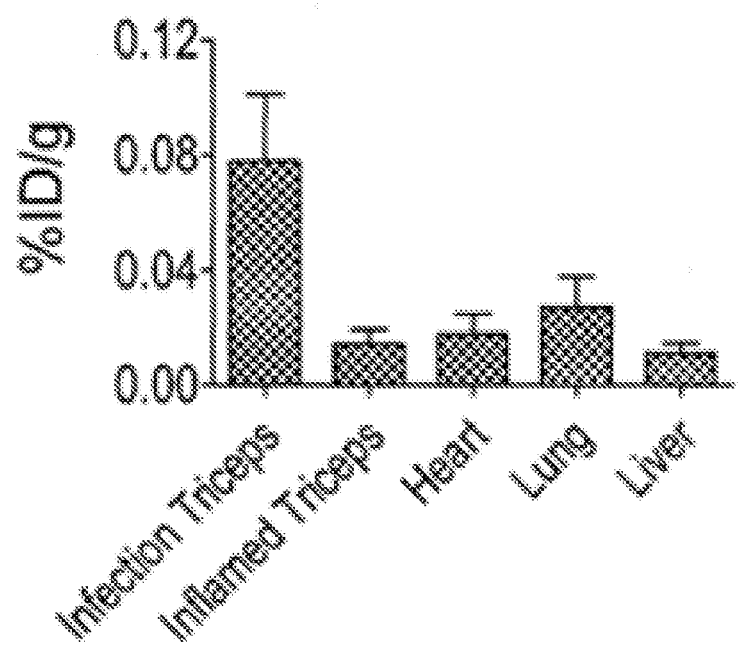
FIG. 3B: Tracer accumulation at different tissues and organs of an infected rat following iv administration of [$^{18}$F]F-PABA.

Example 5. [$^{18}$F]F-PABA does not Accumulate at the Site of Sterile Inflammation One of the main limitations of using FDG to image infection is that FDG accumulates in the mammalian cells involved in the inflammatory response to infection. It was analyzed how inflammation affected the biodistribution of [$^{18}$F]F-PABA by generating an inflammatory response using 50 μL of 1012 CFU of Newman S. aureus heat-killed bacteria. FIG. 3 shows a comparison of levels of [$^{18}$F]F-PABA in the triceps of a rat in which the right triceps is the site of bacterial infection whereas the left triceps is the site of sterile inflammation. Significantly, radiotracer levels are 10-fold higher at the site of infection compared to the site of sterile inflammation, indicating that the accumulation of [$^{18}$F]F-PABA at the site of infection is likely not due to uptake by cells involved in the inflammatory response.

Figure 4A:
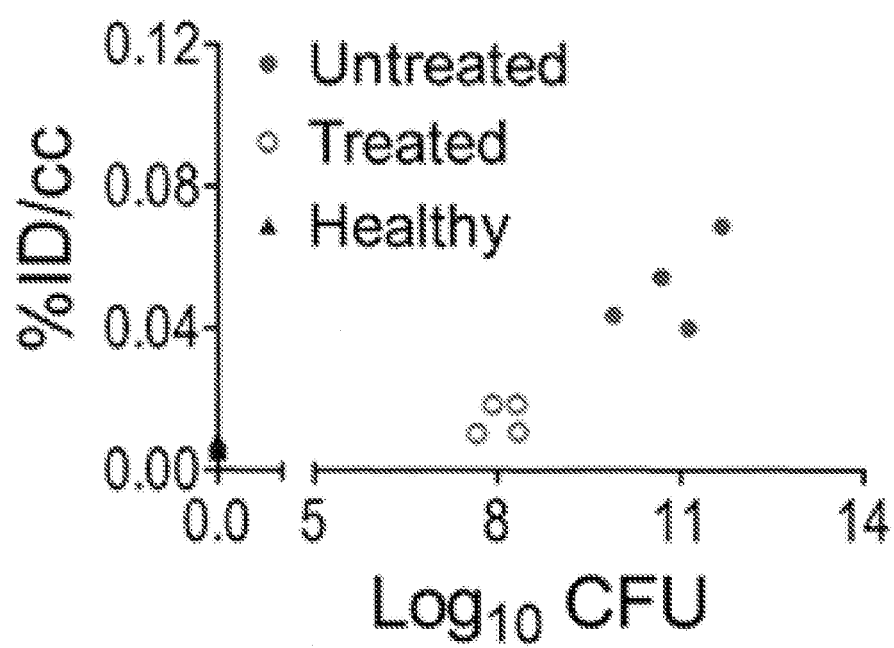
FIG. 4A: Accumulation of tracer in the triceps of an infected rat following antibiotic treatment.
Figure 4B:
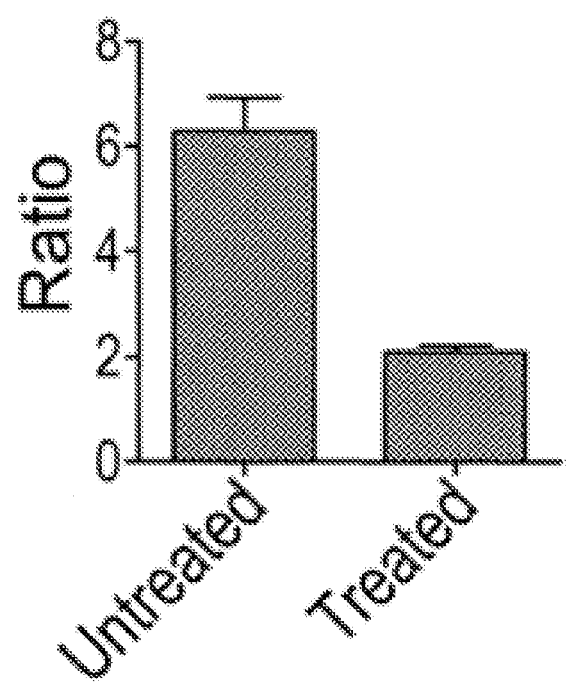
FIG. 4B: Ratio of tracer in infected triceps versus healthy triceps.

Example 6. [$^{18}$F]F-PABA can be Used to Monitor the Change in Bacterial Load Caused by Antibiotic Treatment A key goal is to identify a tracer that can be used to quantify bacterial load and monitor the change in bacterial load during and following antibiotic treatment. In FIG. 4 it is shown that the accumulation of radiotracer in the triceps of an infected rat correlates with bacterial load following administration of vancomycin. The bacterial burden of infected triceps before treatment was 10.8±0.7 Log 10 CFU and showed accumulation of 0.051±0.008% 1 D/cc. After 3 doses of vancomycin, the bacterial burden decreased by almost 3 logs to 8.1±0.3 Log 10 CFU, and resulted in about a 3-fold decrease in tracer levels (0.015±0.005% 1 D/cc). A further 3 doses of vancomycin treatment resulted in an additional 1 log decrease in bacterial burden to 7.0±0.9 Log 10 CFU and similar levels of tracer accumulation of 0.013±0.002% 10/cc). In contrast the tracer levels in the uninfected triceps was 0.007±0.001% 1 D/cc. This data shows that [$^{18}$F]F-PABA can be used to monitor the response to drug treatment and indicates that the limit of detection in this particular model is 7 Log 10 CFU. Healthy bacterial burden found in soft tissue infections in humans (of which S. aureus is the leading cause, accounting for over 60% of all the cases) averages 8.3 Log 10 CFU, showing that 2-[$^{18}$F]F-PABA is sufficiently sensitive to detect clinically relevant infections.

Example 7. Bacterial Infections

An amount of a composition comprising the compound having the structure:

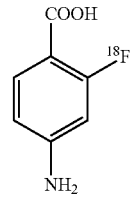

or a salt of the compound; 4-amino-2-[$^{19}$F]-fluorobenzoic acid or a salt of 4-amino-2-[$^{19}$F]-fluorobenzoic acid; and at least one acceptable carrier, is administered to a subject. The location of the composition is detected to determine the presense of an infectious bacteria in the subject.

An amount of a composition comprising the compound having the structure:

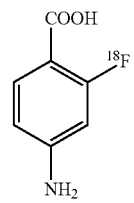 [SMILES: Nc1ccc(C(=O)O)c([18F])c1]

or a salt of the compound; 4-amino-2-[$^{19}$F]-fluorobenzoic acid or a salt of 4-amino-2-[$^{19}$F]-fluorobenzoic acid; and at least one acceptable carrier, is administered to a subject afflicted with a bacterial infection. The location of the composition is detected to determine the location of the infectious bacteria in the subject.

Discussion

The composition, and method of synthesizing the same, described herein contains 2-[$^{18}$F]fluoro-4-aminobenzoic acid ([$^{18}$F]F-PABA), a PET tracer which shows highselectivity for bacteria imaging in soft-tissue rodent models of MSSA, MRSA and E. coli infection. Compared to FDG and other recently developed bacterial infection tracers, [$^{18}$F]F-PABA has several advantages. It is specific for bacterial infection and capable of differentiating infection from sterile inflammation. It shows high signal-to-background ratio in animal infection models. It is able to quantify bacterial burden. It can be produced with high yield using a rapid radiosynthesis method. $^{[18F]}$F-P ABA may also be used applications in bacterial infection diagnosis.

As a bacterial infection tracer which can potentially diagnose infections caused by a broad spectrum pathogens including S. aureus, E. coli, Klebsiella pneumoniae and etc., [$^{18}$F]F-PABA has great commercialization potential. Some infectious conditions caused by S. aureus can serve as good illustrations of the commercialization potential. S. aureus is the leading cause of many different clinically important infections including skin and soft tissue infections, osteomyelitis and infectious endocarditis. Osteomyelitis is the infectious condition of bone, which leads to inflammation and bone necrosis. With an incidence of 21.8 per 100,000 person/years in the United States, osteomyelitis is a serious infectious disease that can result in limb amputation and even death. Indeed, osteomyelitis is the leading cause of non-traumatic amputation in US and worldwide. Osteomyelitis is closely associated with diabetes, a disease that affects 7% of the world's population. Approximately 15% of the diabetic patients would develop foot ulcers in their life time, with an annual incidence of 1 to 4%. Among the diabetic patients with foot ulcers, over 50% would be infected and develop Diabetic foot infections.

Infective endocarditis (IE) is the infection of the endocardial surface of the heart. The estimated incidence rate of IE is 30 to 100 per million person-years, and S. aureus is the causative agent in over half the cases. Despite medical advances, the in-hospital mortality rate of IE is 9.6 to 26%, partly because a definitive diagnosis cannot be reached at an early stage of infection due to the lack of a sensitive diagnostic method. Currently, the diagnosis of IE depends on a combination of microbiological tests and echocardiography together with clinical signs of infection. However, none of these methods provide sufficient sensitivity or specificity to make a rapid and one-step definitive diagnosis.

Patients who are at high risk of these infections are all potential markets of [$^{18}$F]F-PABA. Moreover, the potential of [$^{18}$F]F-PABA is not limited to S. aureus infections. Since our data has already shown that [$^{18}$F]F-PAABA is also able to diagnose E. coli and Klebsiella pneumoniae infections, patients who are suspected of infections caused by these two bacterial species are also potential pool. Besides, due to the existence and essentiality of folate biosynthesis pathway, which incorporates [$^{18}$F]F-P ABA into bacterial cell components, for various bacterial species including Mycobacterium tuberculosis (M. tb), $^{[18F]}$F-P ABA has the commercialization potential of diagnostic tool for such infections.

The composition and method described herein provides a fluorine-18-labeled analog of p-aminobenzoic acid (2-fluoro-4-aminobenzoic acid, F-PABA). F-PABA is a nontoxic substrate (MIC >100 μg/ml) for DHPS and is not toxic to either bacterial or mammalian cells. It has several advantages over FDG and other reported bacterial infection tracers:

1. [$^{18}$F]F-PABA is selectively taken up by live bacteria (MRSA, E. coli and M. tuberculosis) but not mammalian cells;
2. It is specific for bacterial infection, and capable of differentiating infection from inflammation;
3. It can be produced using a rapid radiosynthesis method with high radiochemical yield;
4. It accumulates in a wide range of bacteria, including E. coli, S. aureus and Klebsiella pneumomae;
5. It shows very good signal-to-background ratio in in vivo infection models; and
6. It is capable of quantifying bacterial burden, and therefore can be used to monitor drug treatment efficacy and to assist new antibacterial agent development.

REFERENCES

Bettegowda, C. et al. (2005) Imaging bacterial infections with radiolabeled 1-(2'-deoxy-2'-fluoro-beta-D-arabinofuranosyl)-5-iodouracil. Proc Natl Acad Sci USA 102: 1145-1150.

Chakraborty, S. et al. (2013) Para-Aminosalicylic Acid Acts as an Alternative Substrate of Folate Metabolism in Mycobacterium tuberculosis. 339(6115), 88-91.

Gowrishankar, G. et al. (2014) Investigation of 6-$^{[18F]}$-Fluoromaltose as a Novel PET Tracer for Imaging Bacterial Infection. PLoS One. 9(9), e107951.

Li, Z. B. Et al. (2008) The synthesis of $^{18}$F-FDS and its potential application in molecular imaging. Mol Imaging Biol. 10, 92-98.

Namavari, M. et al. (2015) Synthesis of $^{[18F]}$-labelled Maltose Derivatives as PET Tracers for Imaging Bacterial Infection. Mol Imaging Biol. 17(2), 168-176.

Weinstein, E. A. et al. (2014) Imaging Enterobacteriaceae infection in vivo with $^{18}$F-fluorodeoxysorbitol positron emission tomography. Sci Transl Med. 6(259), 259ra146.

What is claimed is:

1. A composition comprising the compound having the structure:

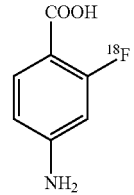

or a salt of the compound; 4-amino-2-[$^{19}$F]-fluorobenzoic acid or a salt of 4-amino-2-[$^{19}$F]-fluorobenzoic acid; and at least one acceptable carrier, wherein the ratio of the 4-amino-2-[$^{18}$F]-flurobenzoic acid to the 4-amino-2-[$^{19}$F]-flurobenzoic acid is in the range from 1:90 to 1:550.

2. The composition of claim 1, wherein the ratio of the 4-amino-2-[$^{18}$F]-fluorobenzoic acid to the 4-amino-2-[$^{19}$F]-fluorobenzoic acid is in a range from 1:324 to 1:500.

3. The composition of claim 1, wherein the ratio of the 4-amino-2-[$^{18}$F]-fluorobenzoic acid to the 4-amino-2-[$^{19}$F]-fluorobenzoic acid is in a range from 1:99 to 1:324.

4. The composition of claim 1, wherein the radiochemical purity of 4-amino-2-[$^{18}$F]-fluorobenzoic acid is at least 95%.

5. The composition of claim 1, wherein the ratio of the 4-amino-2-[$^{18}$F]-fluorobenzoic acid to the 4-amino-2-[$^{19}$F]-fluorobenzoic acid is in a range from 1:99 to 1:500.

* * * * *